United States Patent
Phillips et al.

(12)

(10) Patent No.: US 6,171,793 B1
(45) Date of Patent: Jan. 9, 2001

(54) METHOD FOR SCANNING GENE PROBE ARRAY TO PRODUCE DATA HAVING DYNAMIC RANGE THAT EXCEEDS THAT OF SCANNER

(75) Inventors: Vincent E. Phillips, Sunnyvale; Huu Minh Tran, Milpitas; Thomas Ryder, Los Gatos; Anthony J. Berno, San Jose; Ghassan Ghandour, Atherton, all of CA (US)

(73) Assignee: Affymetrix, Inc., Santa Clara, CA (US)

( * ) Notice: Under 35 U.S.C. 154(b), the term of this patent shall be extended for 0 days.

(21) Appl. No.: 09/294,293

(22) Filed: Apr. 19, 1999

(51) Int. Cl.[7] ........................ C07H 21/04; G01N 33/48
(52) U.S. Cl. ..................... 435/6; 204/403; 536/24.3; 702/19
(58) Field of Search ................ 435/6; 536/24.3; 702/19

(56) References Cited

U.S. PATENT DOCUMENTS

| | | |
|---|---|---|
| 5,143,854 | 9/1992 | Pirrung et al. . |
| 5,316,726 * | 5/1994 | Babson et al. .................. 422/65 |
| 5,545,531 * | 8/1996 | Rava et al. ...................... 435/6 |
| 5,795,716 | 8/1998 | Chee et al. . |

OTHER PUBLICATIONS

Lakowicz "Principles of Fluorescence Spectroscopy" pp. 1–49, Plenum Press, New York 1983.*
Bechtol et al. "Using Dyes and Filters in a Fluorescent imaging System" American Journal of Biotechnology vol. 12, pp. 8–10, 1994.*

* cited by examiner

Primary Examiner—John S. Brusca
Assistant Examiner—Jeffrey S. Lundgren
(74) Attorney, Agent, or Firm—Arter & Hadden, LLP; David G. Alexander, Esq.

(57) ABSTRACT

A genetic sample is analyzed by providing a gene probe array including a plurality of genetic probes having different receptors. The sample is processed to include at least one fluorescently tagged ligand. The array is hybridized by exposing the probes to the processed sample such that ligands can bind to complementary receptors. Composite data having a data dynamic range is obtained from the array using an optical scanner which has a scanner dynamic range that is smaller than the data dynamic range. The scanner optically irradiates and scans the probes and detects fluorescent emissions at a first wavelength which is selected such that the scanner produces valid first data in a low intensity portion of the data dynamic range and is in saturation in at least part of a high intensity portion of the data dynamic range. The scanner then optically irradiates and scans the probes with light and detects fluorescent emissions at a second wavelength which is selected such that the scanner produces valid second data in a high intensity portion of the data dynamic range and is in cutoff in at least part of a low intensity portion of the data dynamic range. A scale factor correlation function is calculated between the first data and the second data, and is applied to convert the second data to have a same scale factor as the first data. The first data for the first portion of the data dynamic range is combined with the converted second data for the second portion of the data dynamic range to obtain the composite data.

24 Claims, 11 Drawing Sheets

METHOD FOR SCANNING GENE PROBE ARRAY TO PRODUCE DATA HAVING DYNAMIC RANGE THAT EXCEEDS THAT OF SCANNER

COPYRIGHT NOTICE

A portion of this patent document contains material which is subject to copyright protection. The copyright owner has no objection to the xerographic reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

The present invention generally relates to the art of biotechnology, and more specifically to a method including scanning a gene probe array to produce data having a dynamic range which exceeds that of the scanner.

2. Description of the Related Art

U.S. Pat. No. 5,143,854, entitled "LARGE SCALE PHOTOLITHOGRAPHIC SOLID PHASE SYNTHESIS OF POLYPEPTIDES AND RECEPTOR BINDING SCREENING THEREOF", issued Sep. 1, 1992 to Michael Pirrung et al, discloses a basic method for synthesizing polypeptide arrays on a substrate by attaching photoremovable groups to the surface of the substrate, exposing selected regions of the substrate to light to activate those regions, attaching an amino acid monomer with a photoremovable group to the activated regions, and repeating the steps of activation and attachment until polypeptides of the desired length and sequence are synthesized. The subject matter of this patent is incorporated herein by reference in its entirety.

The polypeptides of the array are known as "probes" and act as receptors. The probe array is "hybridized" by exposure to a polymer substance which is to be analyzed. The polymer acts as a ligand or target and will bond to one or more probes which have a complementary sequence of bases. The polymer is tagged with a fluorescent reporter group or marker which emits light upon radiation with light of a suitable wavelength. The array is optically scanned by sequentially irradiating the probes in a rectangular pattern and sensing the emitted light intensity at each probe location.

The fluorescent intensity increases with the bonding strength of a ligand to a receptor. Since the probe sequence at each location is known, the unknown polymer ligand can be identified as being complementary to the probe which produces the greatest value of fluorescent intensity.

Improved methods for scanning a probe array are disclosed, for example, in U.S. Pat. No. 5,795,716, entitled "COMPUTER-AIDED VISUALIZATION AND ANALYSIS SYSTEM FOR SEQUENCE EVALUATION", issued Aug. 18, 1998 to Mark Chee et al. The subject matter of this patent is incorporated herein by reference in its entirety.

The methods disclosed in the above referenced patents have been yet further developed to produce a genetic analysis system based on the GeneChip® Probe Array, a product of Affymetrix® of Santa Clara, Calif. The GeneChip includes a large number of polymer probes which are selected to be complementary to an unknown genetic or other material which is to be analyzed. The probes are formed on a substrate in the manner described above, and generally differ from each other by one base. The probe array further includes a protective casing which protects the substrate and attached probes during storage and handling.

The Affymetrix system further includes a fluidics station in which the probe is hybridized by exposure to the genetic or other substance which is to be analyzed. The hybridized array is then tagged with a fluorescent marker and scanned in an optical scanner, and the light intensity at each point is sensed and stored in a digital memory. The data is then processed at a computer workstation to determine the identity of the unknown substance.

The Affymetrix Gene Chip system can be advantageously utilized in a number of biotechnological areas. One of these areas is gene expression analysis. Differential expression data can provide a clear understanding of cellular pathways and identify valuable candidates for drug discovery. GeneChip expression probe arrays simplify genomic research by quantitatively and simultaneously monitoring the expression of thousands of genes.

GeneChip expression probe arrays are capable of identifying mRNA expression level changes of greater than two-fold between experiments and are able to detect mRNA transcripts from the level of only a few copies per cell to more than several hundred thousand copies per cell.

In contrast to prior art spotting methods in which a single clone is used to analyze each mRNA, GeneChip expression arrays use approximately 20 pairs of specific oligonucleotide probes to interrogate each transcript. This probe pairing strategy helps identify and minimize the effects of non-specific hybridization and background signal to enable sensitive and accurate recognition of low-intensity hybridization patterns from mRNA. This makes it possible to specifically detect individual gene transcripts and splice variants and differentiate among closely related members of gene families.

The GeneChip expression arrays contain probes corresponding to a number of reference and control genes. These reference standards make it possible to normalize data from different experiments and compare multiple experiments on a quantitative level.

Another advantageous application of the Affymetrix GeneChip system is polymorphism analysis. This enables researchers to identify and map the thousands of genes comprising the human genome and to identify the base present at specific sequence locations. After the sequences are determined for the first time, it becomes increasingly valuable to identify polymorphisms (or variations) in these genes and to understand how these polymorphisms impact biological function and disease. These association studies require the analysis of DNA samples from a large number of affected and unaffected individuals for each disease under study.

The GeneChip SNP (Single Nucleotide Polymorphism) mapping assays accelerate genetic analysis by minimizing labor, data analysis time and total time required to run complex genotyping studies. The mapping assays enable study of the links between polymorphisms and disease, the mechanisms that lead to disease, and patient response to treatment.

Yet another area in which the Affymetrix GeneChip technology can be advantageously applied is disease management. Researchers are beginning to unravel the mysteries of how genetics impacts human health. The GeneChip technology enables the rapid and accurate analysis of relevant genetic information and has the potential to transform diagnosis into a high-value disease management paradigm.

Disease management is an emerging field focussed on improving the effectiveness of healthcare by using genetic information to improve and guide therapy. Gene expression profiles and polymorphisms that correlate with a specific disease or therapeutic response have the potential to become critical information for disease management.

GeneChip arrays are advantageously applicable in the study of more effective patient management in the areas of infectious disease, cancer and drug metabolism. This enables researchers to understand the genetic basis and progression of disease and patient response to treatment. GeneChip assays are being used to correlate specific mutations with patient outcomes under varied therapeutic drug regimes.

With data gathered through these studies, scientists can develop more detailed prognoses, drug therapies and treatment strategies. Affymetrix has developed the GeneChip CYP450 assay which is the first tool that enables efficient and simultaneous analysis of multiple genotypes associated with drug metabolism defects. These defects can make even innocuous drugs dangerous for certain persons, keeping some potentially valuable therapeutics off the market.

Although the biotechnological applications described above constitute major areas in which the GeneChip system is a desirable analytic tool, these applications are presented as being exemplary only, and not limitatative of the scope of the present invention. On the contrary, the invention as described herein is applicable to numerous and varied arts in which unknown substances are to be identified and, as will be described in detail below, a widely varied range of technologies in which data is to be provided which has a dynamic range larger than a sensor used to obtain the data.

As described briefly above, a hybridized gene probe array is optically scanned by irradiating the individual probes with light of a certain wavelength, and sensing the light intensity resulting from fluorescence of the probes. The ligand polymers of the unknown substance are tagged with fluorescent markers. The markers which are most commonly used are phycoerythrin, which produces maximum or peak fluorescence at a wavelength of 578 nm, and fluorescein, which produces peak fluorescence at a wavelength of 520 nm.

An optical scanner has been developed as a joint project of Affymetrix and the Hewlett Company of Palo Alto, Calif. The scanner is an improvement over previously used scanners and is commercially available from Hewlett Packard under the product designation "HP G2500A Gene Array Scanner". Whereas previously available scanners could only read GeneChip probe arrays with 65,000 probe cells, the Hewlett Packard scanner can read probe arrays with up to 400,000 cells and provide data on thousands of genes and mutations. The scanner focuses a laser beam onto a 3 micron section of a variable size probe array feature, and can detect emitted light at wavelengths of 570 nm and 530 nm for the two common fluorescent markers described above. Note that the "530 nm" setting is a nominal shorthand for using a filter in front of the photomultiplier that permits light of wavelength about 525 nm to 555 nm to pass. Likewise, the "570 nm" setting is a nominal shorthand indicating use of a filter in front of the photomultiplier that allows light of wavelength >570 nm to pass.

In certain applications, however, even the Hewlett Packard scanner is incapable of providing useful intensity readings using conventional markers for very low levels of fluorescent intensity. For this reason, new fluorescent markers are being developed which emit more light and enable useful measurements to be made under conditions which were not previously possible. An example of such a new marker is phycoerythrin-labeled target DNA as will be described in detail below.

Although the greater level of signal obtained was a great boon, it also created a problem. In some cases, the signal intensity was so high that a saturated signal was obtained using the Hewlett Packard scanner. It was not possible to get useful readings at both the high and low ends of the intensity range. This was due to a limitation in the range of detection (dynamic range) of the photomultiplier tube in the Hewlett Packard scanner. Although it is possible to reduce the gain of the tube to prevent saturation, this may result in loss of sensitivity and accuracy at the low end of the range.

In view of the above, a specific need exists in the art for a method of scanning a GeneChip probe array which is hybridized with high intensity fluorescent markers and obtain useful data in both the high and low ranges of the intensity scale. In order to accomplish this goal, it is necessary for the method to produce data having a dynamic range which is greater than that of the scanner itself.

More generally, a need exists in the art for a method of obtaining data from a scanner which is adapted to sense any of a number of varied parameters, and to similarly produce data having a dynamic range which is greater than that of the scanner.

SUMMARY OF THE INVENTION

The present invention provides a method for overcoming the problems which have existed in the prior art. More specifically, a genetic sample is analyzed according to the present invention by providing a gene probe array including a plurality of genetic probes having different receptors. The sample is processed to include at least one fluorescently tagged ligand.

The array is hybridized by exposing the probes to the processed sample such that ligands can bind to complementary receptors. Composite data having a data dynamic range is obtained from the array using an optical scanner which has a scanner dynamic range that is smaller than the data dynamic range. For the purposes of the following description, the data dynamic range will be construed as representing the dynamic range of the measurements resulting from scanning the array.

The scanner optically irradiates and scans the probe arrays with light and detects fluorescent emissions at a first wavelength range which is selected such that the scanner produces valid first data in a low intensity portion of the data dynamic range and is in saturation in at least part of a high intensity portion of the data dynamic range.

The scanner then optically irradiates and scans the probe arrays, detecting light at a second range of wavelengths which are selected such that the scanner produces valid second data in a high intensity portion of the data dynamic range and is in cutoff in at least part of a low intensity portion of the data dynamic range. Of course, it is within the scope of the invention to reverse the order of the two scans.

A scale factor correlation function is calculated between the first data and the second data, and is applied to convert the second data to have a same scale factor as the first data. The first data for the first portion of the data dynamic range is combined with the converted second data for the second portion of the data dynamic range to obtain the composite data. A predetermined analysis procedure is then applied to the composite data.

Although specifically adapted for obtaining expanded dynamic range data obtained from scanning a gene probe array, the invention is also applicable for obtaining data from a scanner which is adapted to sense any of a number of varied parameters, and to similarly produce data having a dynamic range which is greater than that of the sensor itself. Furthermore, the method could be applied to a scanner that does have the ability to select from different available excitation wavelengths.

These and other features and advantages of the present invention will be apparent to those skilled in the art from the following detailed description, taken together with the accompanying drawings, in which like reference numerals refer to like parts.

DETAILED DESCRIPTION OF THE INVENTION

Figure 1:
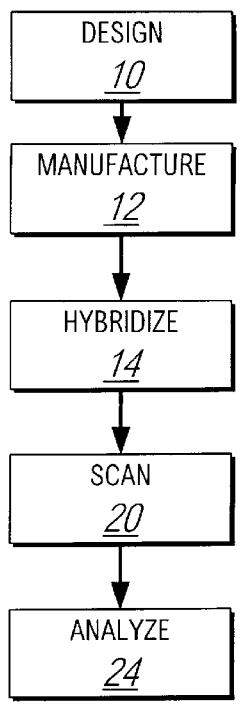
FIG. 1 is a flowchart illustrating a method for analyzing a genetic sample using a gene probe array according to the present invention.

A method of analyzing a sample of unknown nucleic acid or other unknown polymer substance using an Affymetrix GeneChip™ probe array in accordance with a method of the present invention is illustrated in FIG. 1. However, it will be understood that the invention is not limited to this particular application, and can be advantageously utilized in a variety of other, possibly unrelated, technologies.

The first step 10 in the present method is to design a GeneChip probe array for the particular substance which is to be analyzed. A set of oligonucleotide probes to be synthesized is defined, based on their ability to hybridize to the target loci or genes of interest. With this information, computer algorithms are used to design photolithographic masks for use in manufacturing the probe arrays.

In the next step 12, a probe array or arrays is manufactured using a light directed chemical synthesis process, which combines solid-phase synthesis with photolithographic fabrication techniques employed in the semiconductor industry. Using a set of photolithographic masks to define chip exposure sites, followed by specific chemical synthesis steps, the process constructs high-density arrays of oligonucleotides, with each probe in a predefined position in the array. Multiple probe arrays are synthesized on a large glass wafer.

This parallel process enhances reproducibility and helps achieve economies of scale. The wafers are then diced, and individual probe arrays are packaged in injection-molded plastic cartridges, which protect them from the environment and serve as chambers for hybridization.

Figure 2:
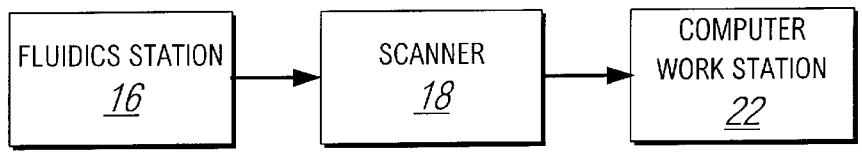
FIG. 2 is a block diagram illustrating the main components of a system for implementing the present method.

Once fabricated, the GeneChip probe arrays are ready for hybridization. In a step 14, the nucleic acid or other unknown substance to be analyzed, in other words the target, is isolated, amplified and labeled with a fluorescent marker or reporter group. The labeled target is then incubated with the array in a fluidics station 16 which is illustrated in FIG. 2.

After the hybridization reaction is complete, the array is inserted into a scanner 18 in a step 20, where patterns of hybridization are detected. The hybridization data are collected as light emitted from the fluorescent reporter groups already incorporated into the target, which is now bound to the probe array. Probes that perfectly match the target generally produce stronger signals than those that have mismatches.

The data obtained by scanning the array with the scanner 18 is processed using a computer work station 22 in a step 24, preferably using a suite of GeneChip analysis software which is available from Affymetrix. Since the sequence and position of each probe on the array are known, by complementarity the identity of the target nucleic acid applied to the probe array can be determined using the analysis software.

Figure 3:
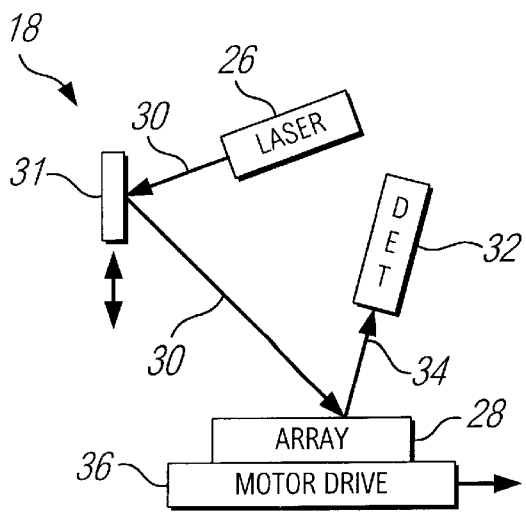
FIG. 3 is a block diagram illustrating the main components of a scanner for scanning a gene probe array according to the invention.

The scanner 18 is preferably the Hewlett Packard GeneArray scanner which was described above. A simplified diagram illustrating the main components of the scanner 18 is shown in FIG. 3. The scanner 18 comprises a laser 26 for illuminating or irradiating a 3 micron spot on a GeneChip probe array 28. A light beam 30 from the laser 26 is reflected from a galvanometrically controlled mirror 31 to the array 28 and causes the probe at the irradiated location to fluoresce if a ligand of the target has bonded thereto.

The fluorescence is created because the targets or ligands are tagged with fluorescent markers or reporters as described above. The intensity of the fluorescent light emitted by a probe increases in accordance with the amount of ligand bound.

The scanner 18 further includes a photodetector 32 which senses light 34 created by fluorescence of the irradiated probe and produces an electronic signal corresponding to the intensity thereof. Although not illustrated in detail, the detector 32 generally includes a photosensor in the form of a photomultiplier tube which senses emitted light, signal processing circuitry for amplifying and shaping the resulting electric signal, and digital processing circuitry and memory for storing numerical values corresponding to the sensed light intensity for each probe.

The laser 26 typically emits light at a fixed wavelength of 488 nm. The detector 32 further includes one or more filters to restrict the wavelengths of light that reach the photomultiplier to certain ranges (e.g. 530 nm or 570 nm).

The scanner 18 further includes a motor drive assembly 36 which is controlled to move the array 28 in a rectangular pattern relative to the laser 26 and detector 32 or vice-versa in synchronization with movement of the mirror 31. This causes the probes of the array 28 to be irradiated and sensed sequentially.

The motor drives for the array 28 and mirror 31 are synchronized with the digital processing circuitry in the detector 32 such that the data obtained by sensing a probe will be paired with the location of the probe on the array 28 in the data stored in the memory. The work station 22 reads the location/intensity pairs of data from the memory in the detector 32 and performs the analytic processing to identify the hybridized nucleic acid or other target substance.

FIGS. 4a to 4i illustrate the manufacturing step 12 for the probe array 28 in greater detail. Although the simplified example which is provided in these drawings illustrates the formation of probe sequences consisting of only two monomers or bases, it will be understood that in practical application the sequences will be considerably longer, with the number of bases being limited only by the photolithographic and algorithm processing technologies described above. Further, not all elements are labeled with reference numerals in all figures to avoid unnecessary cluttering of the drawing.

Figure 4A:
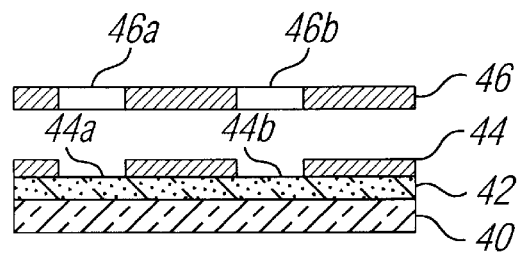
FIGS. 4a to 4i are simplified sectional views illustrating the manufacturing steps of a gene probe array.

FIG. 4a illustrates a substrate 40 having optional linking molecules which are collectively designated as 42 adhered thereto. The substrate 40 is preferably a glass plate, but can be formed of any other suitable material such as described in detail in the above referenced patents to Pirrung and Chee.

If provided, the linking molecules 42 are preferably of sufficient length to permit polymers in a completed substrate to interact freely with molecules exposed to the substrate 40. One linking molecule 42 is bound to the substrate 40 at a corresponding probe location.

The linking molecules may be, for example, aryl acetylene, ethylene glycol oligomers containing 2–10 monomer units, diamines, diacids, amino acids, or combinations thereof. Other linking molecules may be used within the scope of the present invention.

Further illustrated in FIG. 4a are light reactive protector groups which are collectively designated as 44. Each protector group is bound to the free end of a linking molecule 42 or, alternatively, directly to the substrate 40 if the linking molecules are not provided. The protector groups 44 prevent monomers or bases from bonding to the underlying free ends of the linking molecules 42 or to the substrate 40.

The protector groups 44 may be selected from a wide variety of positive or negative light-reactive groups preferably including nitro aromatic compounds such as o-nitrobenzyl derivatives or benzylsulfonyl. Further information on these substances, as well as other exemplary molecules which can be used as protector groups within the scope of the invention, can be found in the above referenced patents to Pirrung and Chee.

The step of FIG. 4a includes positioning a photolithographic mask 46 above the substrate 40. The mask 46 is generally opaque, but is formed with transparent areas or holes 46a and 46b. The substrate 40 as illustrated in FIG. 4a is illuminated or irradiated from above by light of a wavelength selected to de-activate or remove the protector groups 44.

The light is permitted to pass through the transparent areas 46a and 46b and irradiate the protector groups 44 in areas 44a and 44b which underlie the transparent areas 46a and 46b and cause de-activation or removal of the protector groups 44 in these areas. The de-activated protector groups 44a and 44b are illustrated as being removed, although they may remain physically present. The light is blocked by the opaque areas of the mask 46 and does not reach the protector groups 44 which underlie these areas.

Figure 4B:
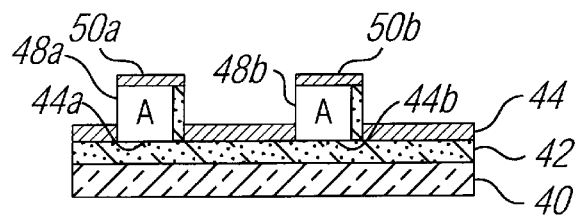

In the next step of FIG. 4b, the substrate 40 and the linker molecules 42 are washed or otherwise exposed to a first monomer "A" as designated by 48a and 48b in the areas 44a and 44b and have protector groups 50a and 50b bonded to their ends. The protector groups 50a and 50b can be the same as or different from the protector groups 44. The monomer "A" bonds to the linker molecules 42 in the areas 44a and 44b, but is prevented from bonding in the other areas by the protector groups 44.

Figure 4C:
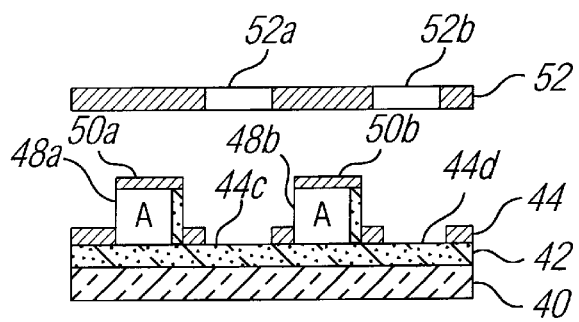
Figure 4D:
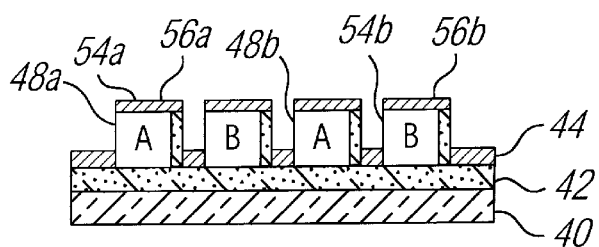

FIG. 4c illustrates providing another photolithographic mask 52 which is formed with transparent areas 52a and 52b in a manner similar to the mask 46. The substrate 40 is illuminated from above to de-activate the protector molecules 44 in areas 44c and 44d which underlie the transparent areas 52a and 53b. The substrate 40 is then exposed to a monomer "B" as illustrated in FIG. 4d which bonds to the linker molecules 42 as indicated at 54a and 54b in the areas 44c and 44d. Protector groups 56a and 56b are bonded to the free ends of the monomer 54a and 54b as described above.

Figure 4E:
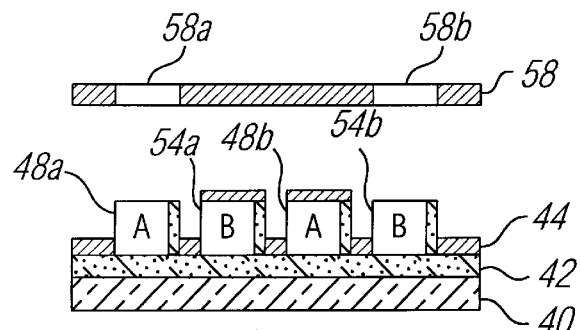
Figure 4F:
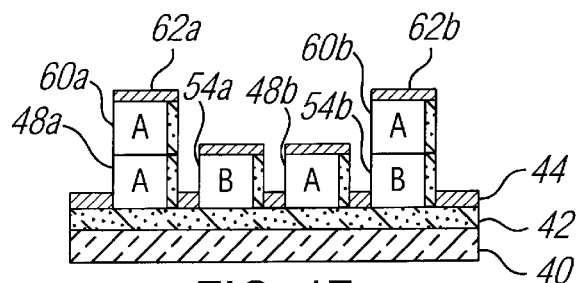

In FIG. 4e, the protector groups 50a and 50b which are bonded to the monomers 48a and 54b are deactivated or removed by light irradiation through a mask 58 having transparent areas 58a and 58b. The substrate 40 is then exposed to the monomer "A" in FIG. 4f such that the monomer "A" bonds to the free ends of the exposed monomers 48a and 54b as indicated at 60a and 60b. Protector groups 62a and 62b are formed on the free ends of the monomers 60a and 60b.

Figure 4G:
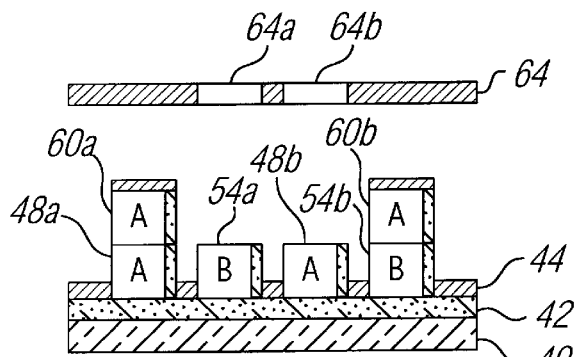
Figure 4H:
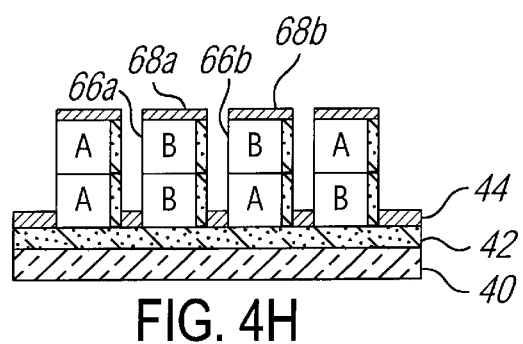

In FIG. 4g, the protector groups on the monomers 54a and 48b are de-activated using light and a mask 64 formed with transparent areas 64a and 64b. The substrate 40 is then exposed to the monomer "B" as illustrated in FIG. 4h to bond the monomer "B" to the monomers 54a and 48b as indicated at 66a and 66b. Protector groups 68a and 68b are bonded to the monomers 66a and 66b.

Figure 4I:
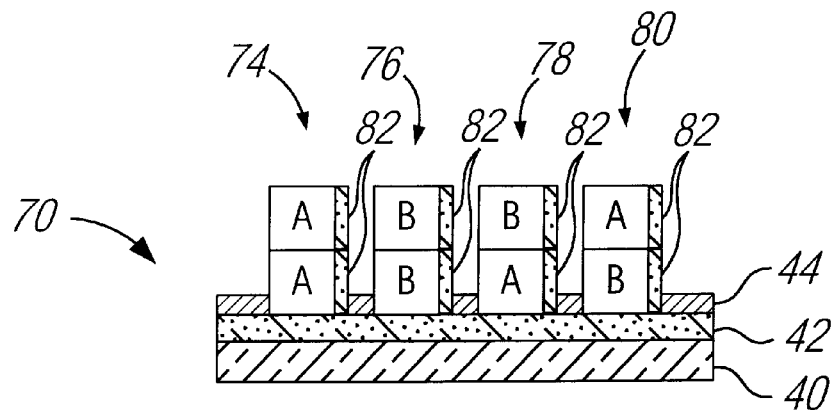
Figure 5:
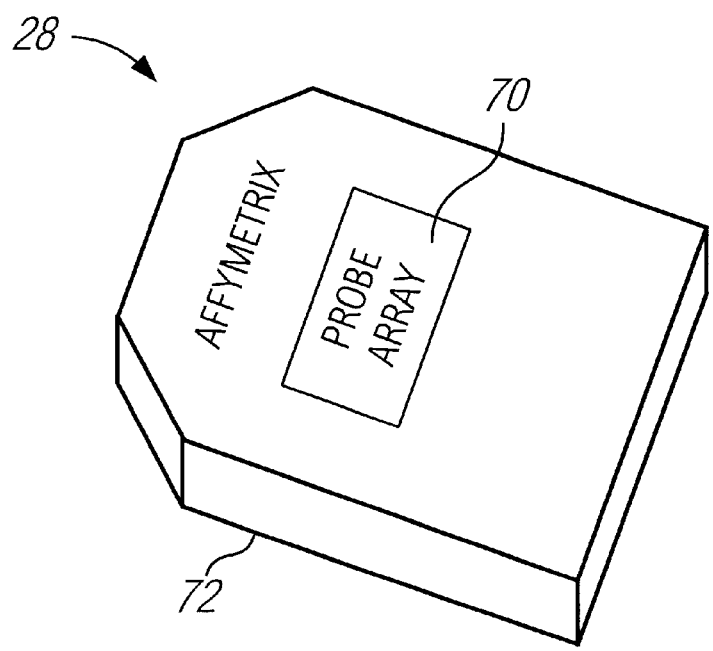
FIG. 5 is a perspective view of a gene probe array.

Finally, as illustrated in FIG. 4i, the protector groups 62a, 62b, 68a and 68b are de-activated or removed. The chip, including the substrate 40 and the elements bonded thereto, is designated as 70 and encapsulated in a protective injection-molded plastic cartridge 72 to constitute the finished GeneChip probe array 28. The cartridge 72 protects the chip 70 from the environment and serves as a chamber for hybridization.

The monomers "A" and "B" are preferably selected from the four main genetic bases, including the purines (a=adenine and g=guanine) and the pyrimidines (c=cytosine and t=thymine), although the invention is not so limited. In the simplified illustration of FIG. 4i, the chip 70 includes the substrate 40, optional linking molecules 42, and four different genetic probes or receptors 74, 76, 78 and 80. The probe 74 includes the monomer or base sequence a-a, the probe 76 includes the sequence b-b, the probe 78 includes the sequence a-b and the probe 80 includes the sequence b-a.

As further illustrated in FIG. 4i, each monomer or base has a fluorescent marker or reporter group bonded thereto to enable optical sensing of the array in the manner described above. These markers are collectively designated as 82 for simplicity of illustration.

Figure 6:
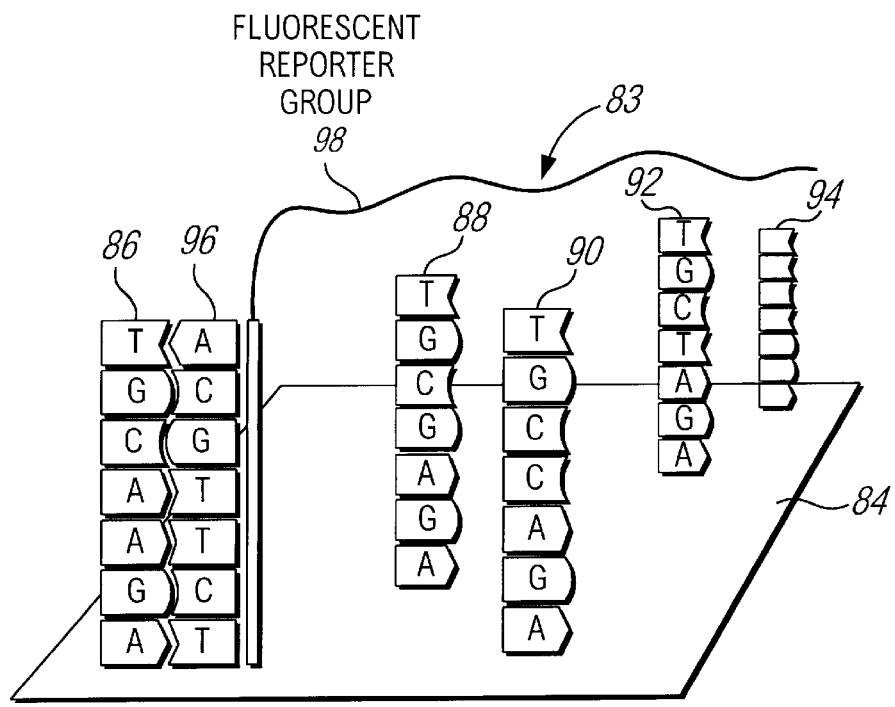
FIG. 6 is a simplified perspective view illustrating a hybridization step of the present method.

The hybridization step 14 is illustrated in simplified form in FIG. 6. A probe array 83 includes a substrate 84 having a plurality of probes or receptors 86, 88, 90, 92 and 94 bonded thereto in the manner described above. Each probe has a different base sequence. The array 83 is exposed to a target or ligand substance 96 having a base sequence which is complementary only to the probe 86. The ligand 96 bonds only to the probe 86 and has a fluorescent marker or reporter group 98 bonded thereto. Upon scanning, only the hybridized probe 86 with the ligand 96 bonded thereto will emit fluorescent light.

Figure 7:
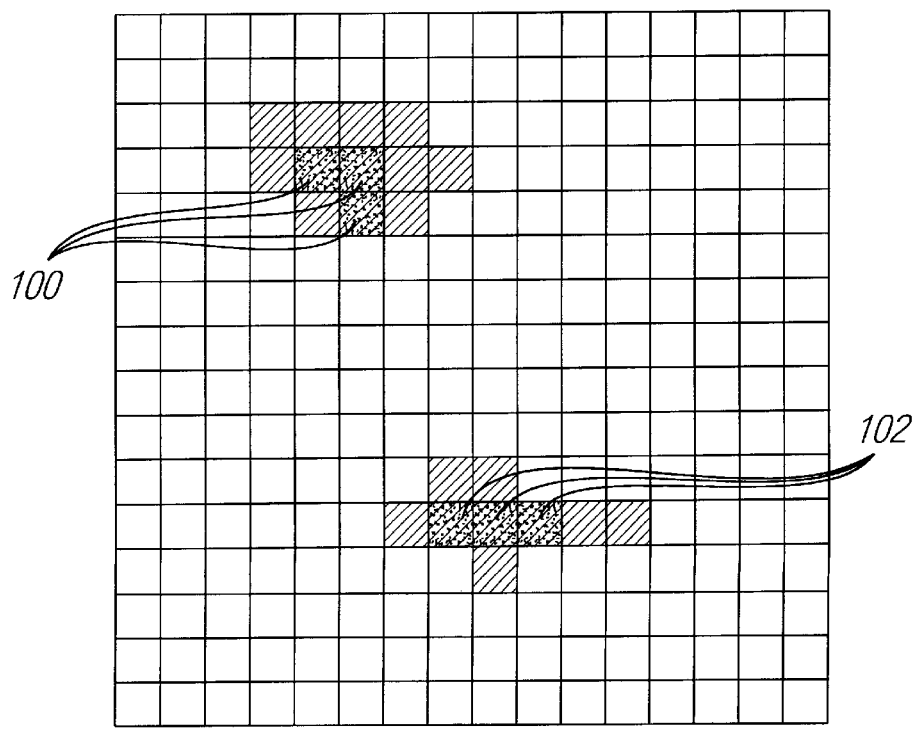
FIG. 7 is view illustrating part of a visual display obtained from scanning a gene probe array including areas in which the scanner was saturated.

As presented above, the scanner 18 may not have sufficient dynamic range to produce valid data at the high and low ends of the intensity range when the amount of hybridizable target bound ranges over several thousandfold and very brilliant labels, such as phycoerythrin, with or without signal amplification, are used to maximize detection sensitivity. FIG. 7 illustrates a portion of a display of probe intensities on a video monitor of the computer work station 22, whereas each square corresponds to many copies of a single probe sequence. In FIG. 7, the darkness of a square as indicated by progressively finer hatching increases as the sensed light intensity increases.

In the figure, there are two areas 100 and 102, each consisting of three dark squares, in which the sensed intensity exceeds the capacity of the scanner 18. The light emitted by the probes in these areas was so intense that the detector 32 in the scanner 18 was saturated. Once the saturation level is reached, any probes which emit light intensities that exceed the saturation level will produce a saturated, constant value.

Figure 8A:
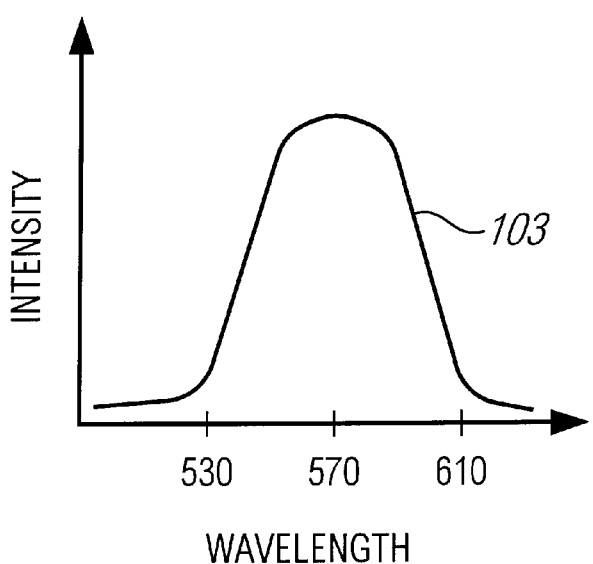
FIGS. 8a and 8b are graphs illustrating the saturation which caused the display of FIG. 7.
Figure 8B:
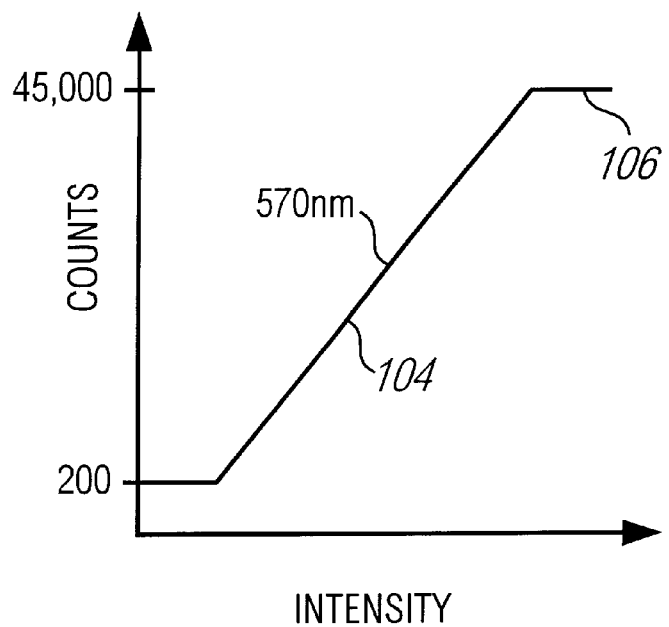

FIG. 8a illustrates the sensed light intensity detected at a wavelength range centered on 570 nm. A curve 103 has a maximum value at 570 nm, and a bell shape which decreases to much lower values at 530 nm and 610 nm. FIG. 8b illustrates the output of the scanner 18 when set to operate at a detection wavelength of >570 nm. Although an optical scanner can generate an analog voltage output having a value corresponding to sensed light intensity, and the scope of the invention includes the use of such a scanner, the Hewlett Packard scanner 18 uses a photomultiplier tube as a sensing element which produces digital pulses or counts. The scanner 18 is calibrated to produce a predetermined number of counts, e.g. 3 counts, for each sensed photoelectron (photon) of light.

As viewed in FIG. 8b, the output of the photomultiplier and associated circuitry in the scanner 18 varies from a background level of, for example, 200 counts (no sensed photons) to a saturation level of, for example, 45,000 counts. The dynamic range of the scanner therefore has an exemplary value of slightly less than 45,000 counts.

As the sensed light intensity increases, the sensor output increases in a generally linear manner from the background level to the saturation level in a curve region 104, and then is clamped to the saturation level of about 45,000 counts in a curve region 106. Thus, although valid data is obtained at the low end of the scanner's dynamic range (low sensed light intensities), at least partially invalid data is obtained above the intensity at which the scanner saturates.

In an exemplary application involving greatly amplified fluorescent markers, it will be assumed that the maximum sensed light intensity would produce an output of 250,000 counts if the scanner had sufficient dynamic range. The present invention provides a method which enables a scanner having a scanner dynamic range extending to, for example, 45,000 counts to produce valid data having a data dynamic range extending to, for example, 250,000 counts. The manner in which the invention overcomes the inherent limitations of the scanner and accomplishes this goal will be described in detail below.

Figure 9:
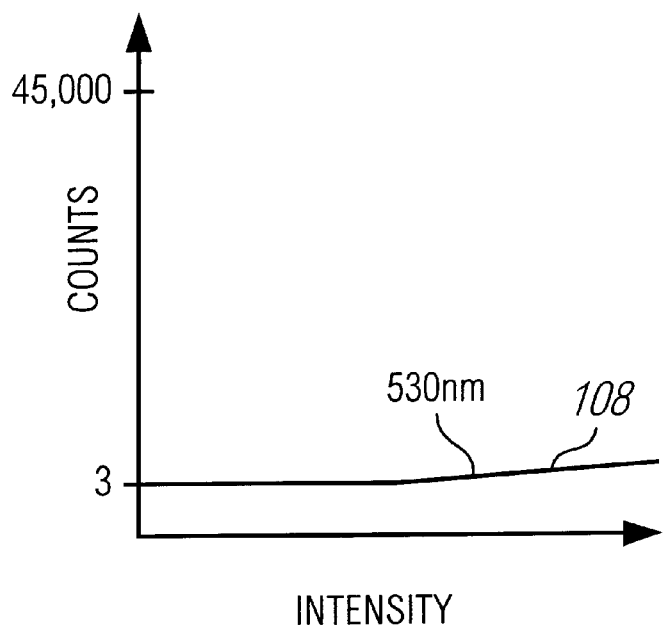
FIG. 9 is a graph illustrating off-peak scanning of the array.

As described above, the scanner 18 is capable of selecting the wavelengths of light detected to be at a wavelength of either 570 nm or 530 nm, corresponding to the peak emission wavelengths of the two common conventional fluorescent markers. It will be assumed that the improved marker as discussed with reference to FIGS. 7 and 8 produces a much higher sensor output at 570 nm than at 530 nm. For example, as illustrated by a curve 108 in FIG. 9, detection at 530 nm produces a curve which is in cutoff for low light intensities, but contains valid data in the high intensity region in which the 570 nm scan was saturated.

Figure 10:
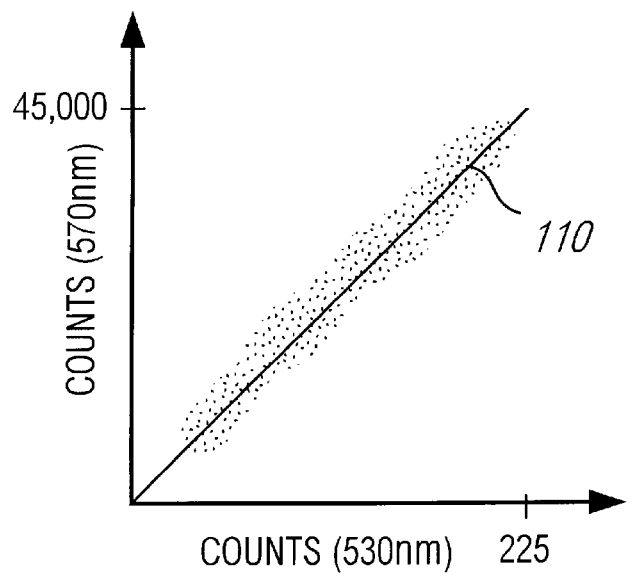
FIG. 10 is a graph illustrating a substantially linear scale factor correlation function linking the graphs of FIGS. 8 and 9.

FIG. 10 illustrates a plot of the sensed intensities of all probes on an array at 570 nm and 530 nm. The count values for 570 nm are plotted on the vertical scale, whereas the count values for 530 nm are plotted on the horizontal scale. It will be seen that the plotted values generally define a curve 110 which can be considered as a scale factor correlation function. The curve 110 is generally linear, but can vary somewhat from linearity.

The lower count values for the 530 nm curve result from off-peak detection. The fluorescent markers emit much less light at 530 nm than at 570 nm. However, the counts for the two wavelengths are related to each other as illustrated in FIG. 10.

Assuming that a particular probe emits light at an intensity at which the scanner 18 just saturates at 570 nm, the count value will be 45,000. Scanning the same probe at 530 nm will produce a count value of, for example, 225. The ratio of the two count values is 45,000/225=200. Thus, a valid intensity value in the 570 nm curve has a value which is approximately 200 times greater than a valid intensity value in the 530 nm curve for the same probe.

The 570 nm and 530 nm curves can be assumed to each have a scale factor. If the scale factor of the 530 nm curve as assumed to be unity and the curve 110 is linear, the scale factor of the 570 nm curve will be approximately 200. The scale factor correlation function as defined by the curve 110 is therefore 200:1=200. In this manner, a valid intensity value or count from the 530 nm curve can be extrapolated to the 570 nm curve by multiplying the count for the 530 nm curve by the scale factor correlation function of 200.

If this is done, the 530 nm curve will be converted and will overlap the 570 nm curve for all valid data points. In a practical application in which the curve 110 is non-linear, the scale factor correlation function will have a different value (varying somewhat from 200) for each 530 nm count value.

Figure 11A:
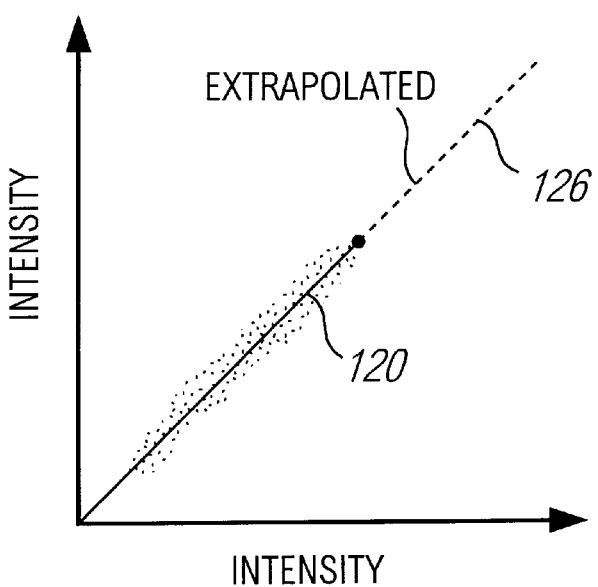
FIGS. 11a and 11b are graphs illustrating extrapolation of data according to the present invention.
Figure 11B:
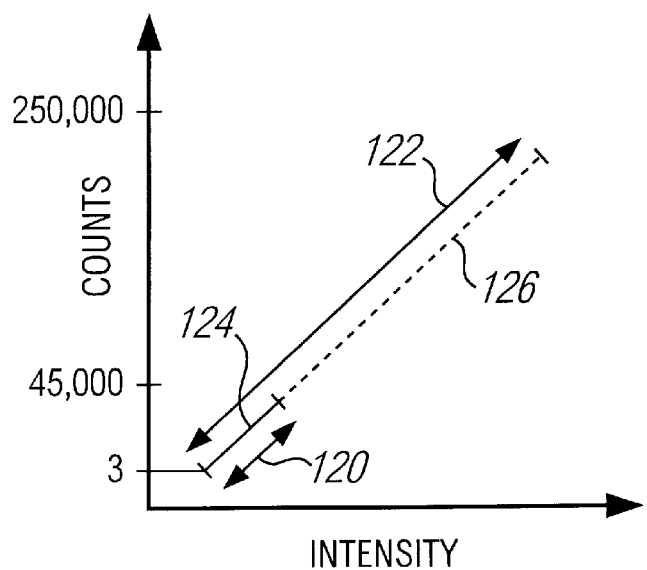
Figure 12:
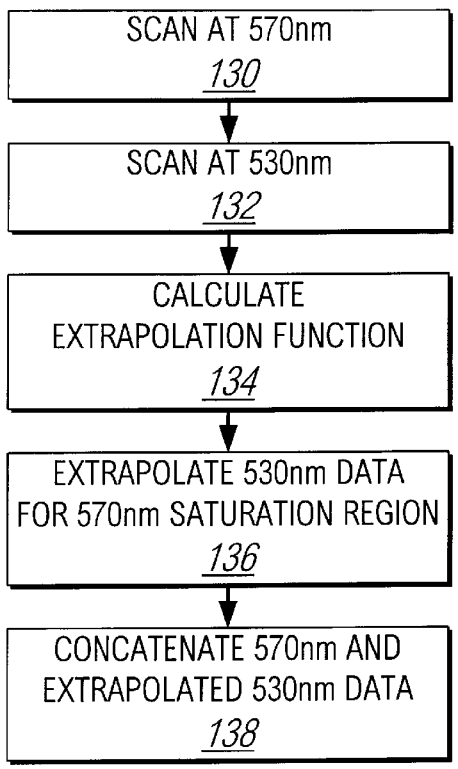
FIG. 12 is a flowchart illustrating a method for obtaining composite data according to the invention.

FIGS. 11a, 11b and 12 illustrate how the above described principles can be used to extend the dynamic range of the scanner 18. As indicated by a step 130 in FIG. 12, a probe array is scanned at a detection wavelength of 570 nm to obtain first data. Then, the array is scanned at a detection wavelength of 530 nm in a step 132 to obtain second data. Of course, it is within the scope of the invention to reverse the order of the scan.

Then, in a step 134, an extrapolation or scale factor correlation function is calculated. Preferably, the ratio of the first and second data or count values for each scanned probe is calculated.

Then, an appropriate curve fitting algorithm is applied to the ratio values to obtain the scale factor correlation function. Assuming that the scale factor for the 530 nm (second) data is taken as unity, the scale factor correlation function will correlate ratio as a function of 530 nm count data. For each count value for the 530 nm scan, the scale factor correlation function will define a scale factor correlation value by which the 530 nm count data can be multiplied and have the same count value as for the 570 nm scan.

Next, as indicated by a step 136, the scale factor correlation function is used to extrapolate or convert the second data for the 530 nm scan to have the same scale factor as the first data for the 570 nm scan. The first and converted second data will have the same values in valid data regions, but will differ in cutoff, saturation and other invalid data regions.

Finally, as indicated by a step 138, the extrapolated or converted data for the 530 nm scan in the saturation region of the 570 nm scan is concatenated to the valid data of the 570 nm scan to provide composite data having a data dynamic range which is larger than a scanner dynamic range of the scanner 18.

As illustrated in FIGS. 11a and 11b, a composite data curve consists of a first portion 120 of the first or 570 nm data and a second portion 126 which is constituted by converted (extrapolated) data from the second or 530 nm data. The second portion 126 is obtained by using the 530 nm count values as the independent variable, and obtaining the converted or extrapolated value as the dependent variable from the scale factor correlation function.

A scanner dynamic range 120 extends from 200 to 45,000 counts, which is the extent of the first portion 124 of the composite curve. The data dynamic range extends from 3 to 250,000 counts, which is the extent of the concatenated first portion 124 and second portion 126. The second portion 126 preferably extends from the first portion 124 in a continuous manner.

Figure 13:
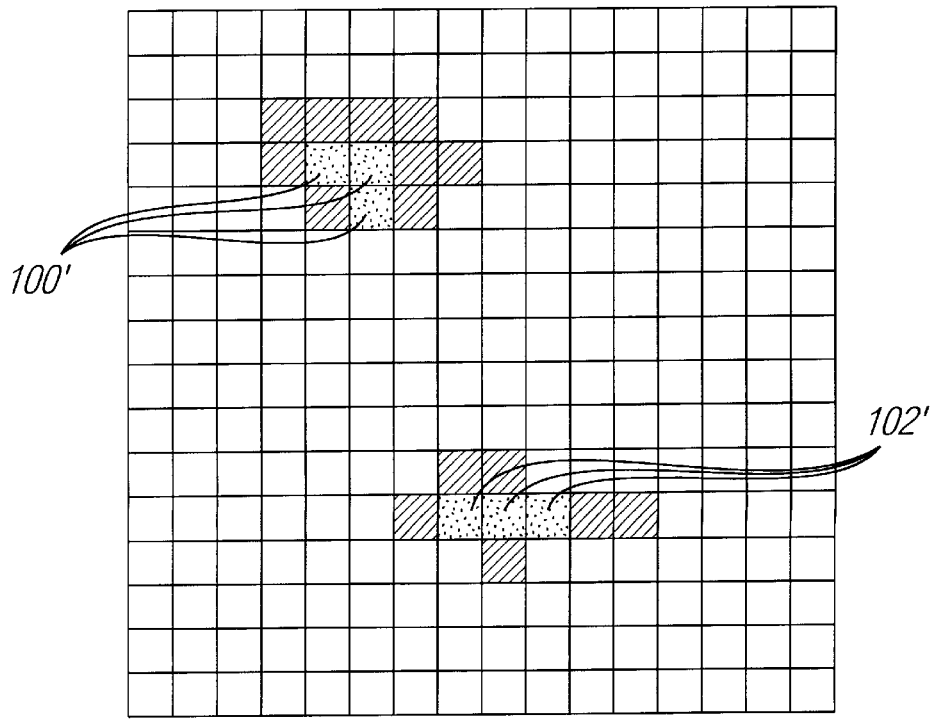
FIG. 13 corresponds to FIG. 7, but illustrates the saturation as being eliminated.

The result of performing the present invention is illustrated in FIG. 13. Assuming that the probes in the areas 100 and 102 emitted intensities between 45,000 and 250,000 counts (not in excess of 250,000 counts), the display will appear as illustrated in which these areas are not dark as illustrated by the finest hatching of FIG. 7. Instead, the areas appear grey as indicated by coarser hatching at 100' and 102'. The intensity would have to exceed 250,000 counts for these areas to appear dark as in FIG. 7.

As described above, the present invention provides a method for obtaining data having a dynamic range which exceeds that of a scanner used to sense the data, thereby overcoming the problem which has existed in the prior art. The invention is not limited, however, to the particular embodiment described above.

An example of a new fluorescent marker system for which the present invention thrust is especially applicable is disclosed in U.S. patent application Ser. No. 60/102,577, entitled "METHODS AND COMPOSITIONS FOR AMPLIFYING DETECTABLE SIGNALS IN SPECIFIC BINDING ASSAYS", filed Sep. 30, 1998 by Martin Goldberg et al. This application is incorporated by reference herein in its entirety.

The marker system provides "signal amplification" by causing more than one fluorescent label or marker to bind to a probe. The system is based on biotinylated streptavidin.

Figure 14A:
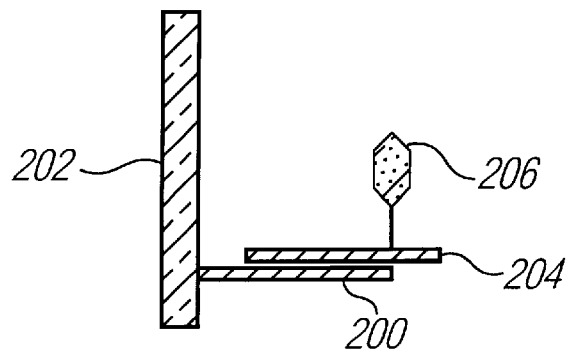
FIGS. 14a to 14d are diagrams illustrating signal amplification using biotinylated streptavidin.

As illustrated in FIG. 14a, a nucleic acid or other probe 200 is bound to a substrate 202 in the manner described above. A nucleic acid or other biotinylated ligand or target 204 is bound to the probe 200. A binding ligand consisting of biotin 206 is attached to the nucleic acid matrix of the ligand 204 by hybridization of a plurality of biotinylated nucleic acids to single strands of the matrix.

The biotin 206 is bound to the ligand 204 prior to hybridization. Thus, FIG. 14a illustrates the configuration of immediately following hybridization.

Figure 14B:
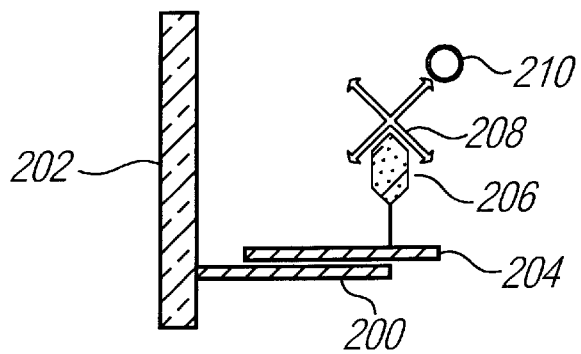

In FIG. 14b, the substrate 202 is exposed to a solution including a receptor in the form of labeled streptavidin 208 which binds to the biotin 206. The streptavidin 208 is labeled with a fluorescent label or marker 210 which can be, for example, fluorescein, phycoerythrin, rhodamine, resorufin, or a coumarin. The specific wavelengths selected for detection depend on the particular marker 210 used.

Figure 14C:
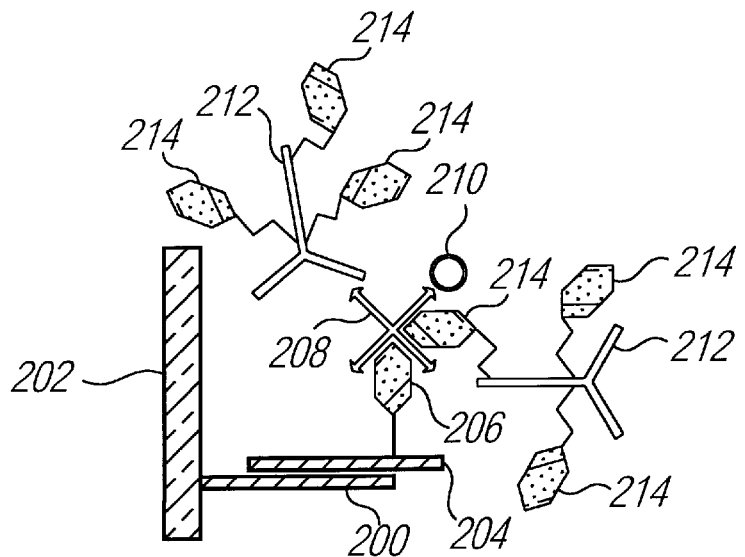

In FIG. 14c, the substrate is exposed to an amplification reagent including biotinylated anti-streptavidin 212, each molecule of which has a plurality of binding ligands covalently bonded thereto. The binding ligands are, in this embodiment, biotin 214. The streptavidin 208 will bond to either the anti-streptavidin 212 itself or to one of the biotins 214 which is carried thereby.

Figure 14D:
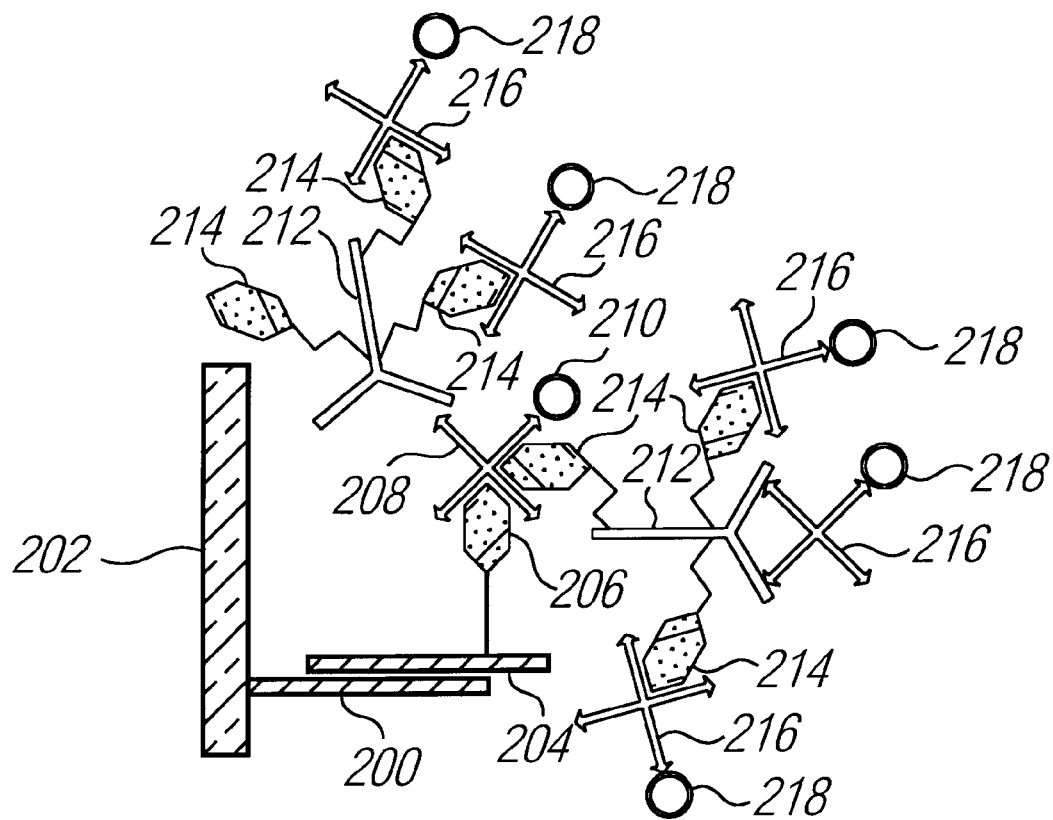

In FIG. 14d, the substrate 202 is exposed to another solution of labeled streptavidin 216 which carries a label or marker 218 as in FIG. 14b. As viewed in the figure, the streptavidin 216 will bond to either the anti-streptavidin 212 or the biotin 214 of the amplification reagent.

In this manner, the number of fluorescent labels or markers which bond to a single probe is multiplied or amplified, thereby providing greater signal intensity upon scanning. In the illustrated example, six fluorescent labels 210 and 218 are bound to the ligand 204 and thereby to the probe 200, as compared to one label 210 in the conventional manner.

The signal amplification process of FIGS. 14a to 14d can be modified by combining several steps. For example, labeled streptavidin can be bonded to the ligand 204 prior to hybridization such that the result of the hybridization step will appear as in FIG. 14b. This omits the step of FIG. 14a.

Another alternative is to provide a solution including molecules of labeled streptavidin and biotinylated anti-streptavidin which are bound together and expose the substrate to this solution after hybridization. This will omit the steps of FIGS. 14b and 14c. It is also possible to expose the substrate to this solution during hybridization, in which case the step of FIG. 14a will also be omitted.

In the above description, it was assumed that the scanner was in cutoff at 530 nm at the low intensity end of its dynamic range, and in saturation at 570 nm in the high intensity end of its dynamic range. It is technically possible to reduce the sensitivity of the scanner at 570 nm or other wavelength such that its dynamic range coincides with the larger data dynamic range. However, this could considerably reduce the resolution of the data, especially at the low end of the curve.

In this context, the present invention is also applicable to a situation in which the scanner is not in cutoff and/or saturation in one or both of the two scans, but it is desired to increase the data dynamic range without reducing the resolution. The present method performed as described above will provide this ability. It is also within the scope of the invention to provide three or more scans with the wavelength or other parameter at suitably selected different values.

Various modifications will become possible for those skilled in the art after receiving the teachings of the present disclosure without departing from the scope thereof.

For example, the wavelengths of 570 nm and 530 nm should be considered as exemplary only, and not limitative of the scope of the invention. Other wavelengths can be used depending on the constraints of a particular application. It is further within the scope of the invention to irradiate and scan the array with different wavelengths of light.

As another exemplary alternative, the scale factor correlation function can be calculated using the 570 nm data as the independent variable (having a scale factor of unity) rather than the 530 nm data. In this latter case, the scale factor correlation function, for a linear curve 110, would be 1/200 or 0.005.

Furthermore, the invention is not limited to scanning a gene chip probe array, or an array which fluoresces upon irradiation with light. The invention can be applied to, for example, scanning an infrared or ultraviolet image, or an image or array of any appropriate type which can be scanned or independently emits light or any other type of electromagnetic or other radiation. The invention can be applied in any environment in which scanning can be performed with a wavelength or any other suitable parameter selected at two or more different values for two or more scans.

The principles of the invention can be further applied to biotechnology or other technical fields in which it is desired to obtain data having a dynamic range which is larger than that of the sensor used to sense the data. For example, a sample under test can be scanned using electromagnetic energy at a frequency which is ramped from one value to another, and the electrical resistance or other parameter sensed. A first scan can be performed at one temperature, whereas a second scan can be performed at a different temperature.

In this case, the parameter which is selected to have different values for the two scans is temperature rather than wavelength as in the above example. Furthermore, rather than scanning a plurality of locations on the sample, the sensor senses an output parameter from the entire sample at two points thereon, and the scanning is performed by varying the input parameter.

What is claimed is:

1. A method for obtaining composite data having a data dynamic range from a sample using a scanner which has a scanner dynamic range that is smaller than the data dynamic range, comprising the steps of:
    (a) using the scanner to scan the sample with a parameter selected at a first value such that the scanner produces valid first data in a first portion of the data dynamic range;
    (b) using the scanner to scan the sample with the parameter selected at a second value which is different from the first value such that the scanner produces valid second data in a second portion of the data dynamic range;
    (c) calculating a scale factor correlation function between the first data and the second data;
    (d) applying the scale factor correlation function to convert the second data to have a same scale factor as the first data; and
    (e) combining the first data for the first portion of the data dynamic range with the converted second data for the second portion of the data dynamic range to obtain the composite data.

2. A method as in claim 1, in which the first and second portions of the data dynamic range are continuous.

3. A method as in claim 1, in which:
    step (a) comprise selecting the first value such that the scanner produces at least partially invalid data in the second portion of the data dynamic range; and
    step (b) comprise selecting the second value such that the scanner produces at least partially invalid data in the first portion of the data dynamic range.

4. A method as in claim 1, in which:
    the first and second values of the parameter are selected such that the first and second data have different values for corresponding locations on the sample.

5. A method as in claim 1, in which:
    the sample has a plurality of locations which produce energy with different corresponding intensities when irradiated;
    steps (a) and (b) comprise controlling the scanner to scan the sample by irradiating the sample and sequentially sensing the intensities.

6. A method as in claim 5, in which the scanner sequentially irradiates the locations.

7. A method as in claim 5, in which:
    the scanner irradiates the locations with electromagnetic radiation; and
    the parameter is a wavelength of the detected electromagnetic radiation.

8. A method as in claim 7, in which the electromagnetic radiation is light.

9. A method as in claim 7, in which:
    the first and second values are selected such that the first and second data have different values for corresponding locations on the sample.

10. A method as in claim 7, in which:
    step (a) comprise selecting the first value such that the scanner is in one of saturation or cutoff at an end of the second portion of the data dynamic range; and
    step (b) comprise selecting the second value such that the scanner is in the other of saturation and cutoff at an end of the first portion of the data dynamic range.

11. A method for obtaining composite data having a data dynamic range from a gene probe array using an optical scanner which has a scanner dynamic range that is smaller than the data dynamic range, the array including a plurality of hybridized probes that fluoresce in response to irradiation by light, the method comprising the steps of:
    (a) using the scanner to optically irradiate and scan the probes with light detected at a first wavelength which is selected such that the scanner produces valid first data in a low intensity portion of the data dynamic range;
    (b) using the scanner to optically irradiate and scan the probes with light detected at a second wavelength which is selected such that the scanner produces valid second data in a high intensity portion of the data dynamic range;
    (c) calculating a scale factor correlation function between the first data and the second data;
    (d) applying the scale factor correlation function to convert the second data to have a same scale factor as the first data; and
    (e) combining the first data for the first portion of the data dynamic range with the converted second data for the second portion of the data dynamic range to obtain the composite data.

12. A method as in claim 11, in which the first and second portions of the data dynamic range are continuous.

13. A method as in claim 11, in which:
    step (a) comprise selecting the first value such that the scanner produces at least partially invalid data in the second portion of the data dynamic range; and
    step (b) comprise selecting the second value such that the scanner produces at least partially invalid data in the first portion of the data dynamic range.

14. A method as in claim 11, in which:
    step (a) comprise selecting the first value such that the scanner is in saturation in at least part of a high intensity portion of the data dynamic range;
    step (b) comprise selecting the second value such that the scanner is in cutoff in at least part of a low intensity portion of the data dynamic range.

15. A method as in claim 11, in which:
    the first and second wavelengths are selected such that the first and second data have different values for corresponding probes.

16. A method as in claim 11, in which:

the probes fluoresce with different corresponding intensities when irradiated;

steps (a) and (b) comprise controlling the scanner to scan the probes by sequentially sensing the intensities.

17. A method as in claim 16, in which the scanner sequentially irradiates the probes.

18. A method for analyzing a genetic sample, comprising the steps of:

(a) providing a gene probe array including a plurality of genetic probes having different receptors;

(b) processing the sample to include at least one fluorescently tagged ligand;

(c) hybridizing the array by exposing the probes to the processed sample such that ligands can bind to complementary receptors;

(d) obtaining composite data from the array having a data dynamic range using an optical scanner which has a scanner dynamic range that is smaller than the data dynamic range by performing the substeps of:

(d1) using the scanner to optically irradiate and scan the probes with light detected at a first wavelength which is selected such that the scanner produces valid first data in a low intensity portion of the data dynamic range;

(d2) using the scanner to optically irradiate and scan the probes with light detected at a second wavelength which is selected such that the scanner produces valid second data in a high intensity portion of the data dynamic range;

(d3) calculating a scale factor correlation function between the first data and the second data;

(d4) applying the scale factor correlation function to convert the second data to have a same scale factor as the first data; and (d5) combining the first data for the first portion of the data dynamic range with the converted second data for the second portion of the data dynamic range to obtain the composite data; and (e) applying a predetermined analysis procedure to the composite data.

19. A method as in claim 18, in which the first and second portions of the data dynamic range are continuous.

20. A method as in claim 18, in which:

step (d1) comprise selecting the first value such that the scanner produces at least partially invalid data in the second portion of the data dynamic range; and step (d2) comprise selecting the second value such that the scanner produces at least partially invalid data in the first portion of the data dynamic range.

21. A method as in claim 18, in which:

step (d1) comprise selecting the first value such that the scanner is in saturation in at least part of a high intensity portion of the data dynamic range;

step (d2) comprise selecting the second value such that the scanner is in cutoff in at least part of a low intensity portion of the data dynamic range.

22. A method as in claim 18, in which:

the first and second wavelengths are selected such that the first and second data have different values for corresponding probes.

23. A method as in claim 18, in which:

the probes fluoresce with different corresponding intensities when irradiated;

steps (d1) and (d2) comprise controlling the scanner to scan the probes by sequentially sensing the intensities.

24. A method as in claim 19, in which the scanner sequentially irradiates the probes.

* * * * *